March 10, 1964 C. FISCHER Plant Pat. 2,375
GLADIOLUS PLANT
Filed Jan. 30, 1963
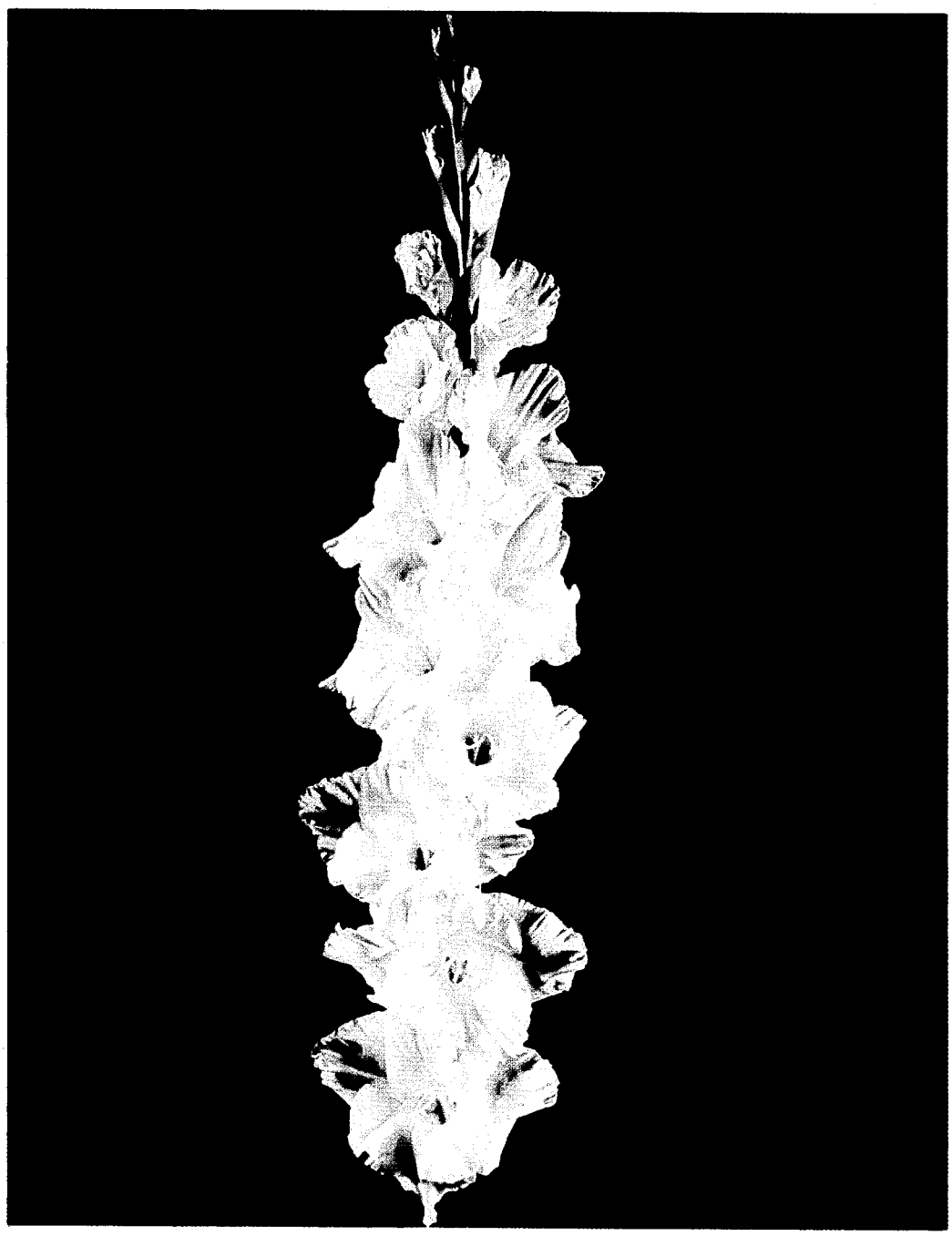
Inventor.
Carl Fischer
By: Robb & Robb
Attorneys.

United States Patent Office

Plant Pat. 2,375
Patented Mar. 10, 1964

2,375
GLADIOLUS PLANT

Carl Fischer, St. Charles, Minn., assignor to Imperial Flowers Limited, Leamington, Ontario, Canada, a corporation of Canada Filed Jan. 30, 1963, Ser. No. 255,141
1 Claim. (Cl. Plt.—85)

The present invention relates to a new and distinct variety of gladiolus plant which was originated by me by crossing the variety known as "Southern Belle" (unpatented) with the variety known as "Campanile" (unpatented), the former being the seed parent and the latter being the pollen parent.

The primary objective of this breeding was to produce a new gladious variety representing an improvement in the variety known as "Andrena" (unpatented). This objective was fully achieved, as evidenced by the following unique combination of outstanding characteristics which distinguish the new variety from its parents, as well as from all other varieties of which I am aware:

(1) The ability to propagate well;

(2) The ability of the flowers to open unusually well from tight buds; and (3) A distinctive and attractive delicate rose general color tonality of the flowers, with ivory white blotches on the lips of the flower petals and in the flower throats, said flowers having the ability to retain and sometimes improve the coloring aforementioned when cut in the tight bud stage.

My new variety resembles the variety known as "Andrena" more than any other, but differs principally therefrom by being more prolific, much taller in its habit of growth, larger flowers, a much better flower opening habit especially when the flowers are cut in the tight bud stage and resulting in more florets being open at once, and a more ruffled flower form.

Asexual reproduction of my new variety by cormels through several generations, as performed by me at St. Charles, Minnesota, shows that the foregoing characteristics and distinctions come true to form and are established and transmitted through succeeding propogations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Chart issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Vigorous; an extremely prolific propagator; average height ranges from about 60 inches to 62 inches.

Blooming habit: An early mid-season bloomer in the Northern latitudes of the United States; comes into bloom from large bulbs in from about 75 to 80 days.

Stems: Slender; willowy.

*Diameter at base.*—About ⅜ inch.

*Color (just above bulb).*—Light purple.

Foliage: Droopy leaves when grown in the field row; leaves average about 40 inches long and range from about 1½ inches to 1¾ inches wide. Color—green.

Disease resistance: Unusually good resistance to Septoria leaf spot, and average resistance to Fusarium yellows and Sclerotinia dry rot, as determined by comparison with other varieties grown in my fields near St. Charles, Minnesota, in irrigated black loam soil.

Corms (bulbs): Round; high-crowned; smooth; average diameter ranging between 2 inches and 2½ inches; husks cover the bulb well and have a purplish cast. Color of flesh—Amber Yellow, Plate 505.

*Flower*

Spike: Tall; willowy; usually bears an average of 20 buds, with 7 or 8 florets opening at once and with 6 or 7 buds showing color.

Bud:

*Size.*—About 2½ inches long when opening.

*Opening.*—One of the best openers from tight bud of all varieties heretofore known; 6 or 7 buds will show color at one time.

Flower:

*Arrangement.*—Florets are semi-formally arranged on the stem and all face forward.

*Size.*—Lower florets average from 5 inches to 5¼ inches in diameter, with upper florets being progressively smaller.

*Form.*—Florets are ruffled, round, wide open and slightly recurved.

*Keeping qualities.*—Unusually good.

Petals:

*Shape.*—Broad; round; ruffled; recurved.

*Size.*—Outer petals—about 2½ inches wide. Lip petal—about 1¾ inches wide.

*Aspect.*—Thin substance.

*Fragrance.*—None.

*Color.*—Color improves when flowers are cut in tight bud stage; general color effect of outer petals is between Amaranth Rose, Plate 530/1 and Amaranth Rose, Plate 530, with inner petals being Amaranth Rose, Plate 530/3 with White blotches on the lips and throat; calyx has small dots of Tyrian Purple, Plate 727.

*Reproductive Organs*

Stamens: Color—nearly white, with gray on edges on bottom surface.

Pistil: Color—Amaranth Rose, Plate 530/2.

I claim:

A new and distinct variety of gladiolus plant, substantially as herein shown and described, characterized particularly as to novelty by the unique combination of a prolific propagating habit, an ability of the flowers to open unusually well from a tight bud stage, and a distinctive and attractive general color tonality of the flowers corresponding to delicate rose shades, with ivory white blotches on the lips of the flower petals and in the flower throats, said flowers having the ability to retain the aforementioned coloring and sometimes to even improve the same, especially when cut in the tight bud stage.

No references cited.